United States Patent
Van Vlierberghe et al.

(10) Patent No.: US 10,571,462 B1
(45) Date of Patent: Feb. 25, 2020

(54) BIOMARKER FOR THE PREDICTION OF PRIMARY NON FUNCTION OF A LIVER GRAFT

(71) Applicant: Universiteit Gent, Ghent (BE)

(72) Inventors: Hans Van Vlierberghe, Zingem (BE); Xavier Verhelst, Landskouter (BE)

(73) Assignee: Universiteit Gent, Ghent (BE)

( * ) Notice: Subject to any disclaimer, the term of this patent is extended or adjusted under 35 U.S.C. 154(b) by 45 days.

(21) Appl. No.: 15/740,678

(22) PCT Filed: Jun. 30, 2016

(86) PCT No.: PCT/EP2016/065383
§ 371 (c)(1),
(2) Date: Dec. 28, 2017

(87) PCT Pub. No.: WO2017/001600
PCT Pub. Date: Jan. 5, 2017

(30) Foreign Application Priority Data

Jul. 2, 2015 (EP) ..................... 15174982

(51) Int. Cl.
*G01N 33/50* (2006.01)
*G01N 27/447* (2006.01)
(52) U.S. Cl.
CPC ....... *G01N 33/5091* (2013.01); *G01N 27/447* (2013.01); *G01N 2800/085* (2013.01); *G01N 2800/245* (2013.01); *G01N 2800/50* (2013.01); *G01N 2800/52* (2013.01); *G01N 2800/56* (2013.01); *G01N 2800/60* (2013.01)
(58) Field of Classification Search
CPC ................................................ G01N 33/5091
See application file for complete search history.

(56) References Cited

FOREIGN PATENT DOCUMENTS

| WO | 2008152070 A1 | 12/2008 |
| WO | 2016065383 A1 | 5/2016 |
| WO | 2017001600 A1 | 1/2017 |

OTHER PUBLICATIONS

Rao et al., Hyaluronate levels in donor organ washout effluents: a simple and predictive parameter of graft viability, Liver, Feb. 1996, pp. 48-54, vol. 16, No. 1.
Laroy et al., Glycome mapping on DNA sequencing equipment, Nature Protocols, Jun. 27, 2006, pp. 397-405, vol. 397, No. 1, Nature Publishing Group, GB.
Blomme et al., N-glycan based biomarker distinguishing non-alcoholic steatohepatitis from steatosis independently of fibrosis, Digestive and Liver Disease, Nov. 25, 2011, pp. 315-322, vol. 44, No. 4.
Verhelst et al., Glycomics as a new tool for preservation fluid analysis in liver transplantation, Acta Gastroenterologica Belgica, Jan. 1, 2013, p. A25.
Verhoeven et al., Biomarkers to assess graft quality during conventional and machine preservation in liver transplantation, Journal of Hepatology, Sep. 1, 2014, pp. 672-684, vol. 61, No. 3.
PCT International Search Report, PCT/EP2016/065383, dated Aug. 18, 2016.
PCT International Written Opinion, PCT/EP2016/065383, dated Aug. 18, 2016.
Vermassen et al., "Urinary Prostate Protein Glycosylation Profiling as a Diagnostic Biomarker for Prostate Cancer," The Prostate, Vo. 75, (2015), pp. 314-322.
Vanderschaeghe et al., "GlycoFibroTest Is a Highly Performant Liver Fibrosis Biomarker Derived from DNA Sequencer-based Serum Protein Glycomics," Molecular & Cellular Proteomics, vol. 8, (2009), pp. 986-994.
Shaw et al., "Hepatic Retransplantation," Transplantation Proceeding, vol. 17, (1985), pp. 264-271.
Oh et al., "Independent Predictors for Primary Non-Function After Liver Transplantation," Yonsei Medical Journal, vol. 45, (2004), pp. 1155-1161.
Monbaliu et al., "Machine Perfusion of the Liver: Past, Present and Future," Current Opinion in Organ Transplantation, vol. 15, (2010), pp. 160-166.
Feng et al., "Characteristics Associated With Liver Graft Failure: The Concept of a Donor Risk Index," American Journal of Transplantation, vol. 6, (2006), pp. 783-790.
Devlin et al., "Relationship Between Early Liver Graft Viability and Enzyme Activities in Effluent Preservation Solution," Transplantation, vol. 60, (1995), pp. 627-631.
Calleweart et al., "Noninvasive Diagnosis of Liver Cirrhosis Using DNA Sequencer-Based Total Serum Protein Glycomics," Nature Medicine, vol. 10, (2004), pp. 429-434.
Callewaert et al., "Total Serum Protein N-Glycome Profiling on a Capillary Electrophoresis-Microfluidics Platform," Electrophoresis, vol. 25, (2004), pp. 3128-3131.
Bronsther et al., "Effluent Levels of Hyaluronic Acid Can Predict Ultimate Graft Outcome After Clinical Liver Transplantation: A Prospective Series," Transplantation Proceeding, vol. 25(1 Pt 2), (1993), pp. 1538-1540.
Braat et al., "The Eurotransplant Donor Risk Index in Liver Transplantation: ET-DRI," American Journal of Transplantation, vol. 12, (2012), pp. 2789-2796.
Blomme et al., "Serum Protein N-Glycosylation in Paediatric Non-Alcoholic Fatty Liver Disease," Pediatric Obesity, vol. 7, (2012), 20 pages.

*Primary Examiner* — Bin Shen
(74) *Attorney, Agent, or Firm* — TraskBritt

(57) ABSTRACT

This disclosure relates to the technical field of liver transplantation and discloses a set of biomarkers that can be used to assess the quality of the liver graft before transplantation. More specifically, this disclosure describes a process of predicting the appearance of primary non function (PNF) of a liver graft via determining the relative abundance of the undergalactosylated glycans in the perfusate N-glycome of the liver before transplantation.

13 Claims, 9 Drawing Sheets

NGA2F   NGA2FB   NG1A2F

■ : N-acetylglucosamine   ● : mannose   ○ : galactose   ▲ : fucose

- PRIOR ART -

BIOMARKER FOR THE PREDICTION OF PRIMARY NON FUNCTION OF A LIVER GRAFT

CROSS-REFERENCE TO RELATED APPLICATIONS

This application is a national phase entry under 35 U.S.C. § 371 of International Patent Application PCT/EP2016/065383, filed Jun. 30, 2016, designating the United States of America and published in English as International Patent Publication WO 2017/001600 A1 on Jan. 5, 2017, which claims the benefit under Article 8 of the Patent Cooperation Treaty to European Patent Application Serial No. 15174982.7, filed Jul. 2, 2015.

TECHNICAL FIELD

This application relates to the technical field of liver transplantation and discloses a set of biomarkers that can be used to assess the quality of the liver graft before transplantation. More specifically, this application discloses a process of predicting the appearance of primary non function (PNF) of a liver graft via determining the relative abundance of the undergalactosylated glycans in the perfusate N-glycome of the liver before transplantation.

BACKGROUND

Liver transplantation is the only curative treatment for end-stage liver disease, acute liver failure and selected patients with liver cancer. Every year, more than 20,000 liver transplantations are performed worldwide and this activity is concentrated in the Western world using cadaveric organ donors.

A rare but potentially fatal complication after liver transplantation is PNF. PNF is defined as the absence of initial function following transplantation. Such evidence would include not only frank signs of total hepatic failure (e.g., profound hypoglycemia, uncorrectable coagulopathy, stage IV coma, renal failure, acidosis, and cardiodynamic shock), but also other signs of irreparable damage to the organ (i.e., massive rises in transaminases along with unrelenting daily rises in bilirubin, persistent renal insufficiency, mental confusion and persistent coagulopathy). The only treatment is an urgent retransplantation within 24-48 hours.[1] The incidence of PNF ranges from 2% to 10% and is responsible for 36% of retransplantation. PNF is associated with a female recipient, steatosis of the donor liver graft and an increased cold ischemia time.[2]

Thus, there is a need to predict the occurrence of PNF based on assessing the quality of the donor liver.

The current strategy for donor organ "selection" is based on a clinical assessment of the donor organ using clinical parameters including age, sex, race, comorbidity, cause of death, biochemical values (liver enzymes), allocation and donor type and ischemia time. Based on these parameters, a Donor Risk Index[3] has been developed, with an adaptation for the Eurotransplant region (the Eurotransplant DRI (ET-DRI)),[4] that provides an estimation of possible graft dysfunction, but not a formal assessment of graft quality. Moreover, DRI is often not predictive of PNF.

Biomarkers for viability have been studied in liver tissue (necessitating a liver biopsy) or perfusate. Perfusate samples are easy to collect and, in contrast to a liver biopsy that only represents a small part of the liver, represent the global liver function. In this regard, perfusate has been studied for decades in order to predict organ failure after liver transplantation. Previous reports propose AST, a routinely used liver enzyme, as a marker for graft viability.[5] However, sensitivity and specificity are insufficient. Other authors reported hyaluronic acid in perfusate as a marker for PNF, with a high negative predictive value for the appearance of PNF.[6] Other experimental biomarkers in perfusate have been proposed using HDmiR, hepatocyte-derived miRNA, but are focused on other outcome parameters than PNF.[7]

A new strategy to increase the quality of donor organs is the use of machine perfusion rather than cold storage. During transport, the organ vessels are perfused actively, which could improve outcome of the organ and also increase the donor organ pool.[8] However, the use of machine perfusion increases the need for reliable biomarkers to assess organ viability during and after perfusion.

In addition to the use of machine perfusion, a decreasing organ quality and an increasing demand for liver transplantation necessitate a search for a robust biomarker for liver graft quality.

The glycome is defined as the mixture of carbohydrate structures present in a biological sample. When these glycan structures are linked to an asparagine residue of proteins, it is defined as the N-glycome. In the early years of 2000, Callewaert et al.[9] developed a platform for high-throughput and high-sensitivity quantitative profiling of the N-glycome, using a DNA fragment analysis equipment (common in molecular genetics laboratories). This technique was successfully applied to analyze the serum N-glycome and led to the development of biomarkers for liver cirrhosis (GlycoCirrhoTest),[10] liver fibrosis (GlycoFibroTest),[11] and non alcoholic steatohepatitis (GlycoNashTest).[12,13]

Verhelst et al.[14] further disclosed glycomics as a tool for preservation fluid analysis in liver transplantation. These authors demonstrate that electropherograms or N-glycome profiles of liver perfusate before engraftment show an important similarity with electropherograms or N-glycome profiles of serum of healthy human volunteers.

Verhoeven et al.[7] disclose that PNF of liver graft during machine preservation can be assessed by determining the degree of graft steatosis. Blomme et al.[12] disclose that glycan-based biomarkers can be used to measure the presence and degree of lobular inflammation in patients with non-alcoholic steatohepatitis (NASH). However, the latter biomarker is clearly not a marker of the presence of steatosis as is confirmed by the data presented in this disclosure. Moreover, the latter authors determined that N-glycans is in the serum—not in perfusate—of non-alcoholic fatty liver disease patients.

Taken together, the existence of a robust and reliable glycomarker, which can be used to predict PNF, has not been described nor suggested.

BRIEF SUMMARY

Disclosed is a new approach for the estimation of liver graft quality based on the N-glycan analysis of perfusion fluid (also called perfusate) in which the liver was transported.

Indeed, the disclosed is a study with a cohort of 54 liver transplantations wherein three patients developed PNF: all three PNF patients had a marked up-regulation of NGA2F (agalactosylated, core-α-1,6-fucosylated biantennary N-glycan) that could significantly discriminate them with 100% accuracy from non-PNF patients.

In these patients, an increase was also observed in the relative abundance of other undergalactosylated glycans in the perfusate glycome including NGA2FB (agalactosylated, core-α-1,6-fucosylated bisecting biantennary N-glycan) and NG(1)A2F (mono galactosylated, core-α-1,6-fucosylated biantennary N-glycans).

Hence, measurement of the glycomarker(s) NGA2F and/or NGA2FB and/or NG1A2F assesses donor graft quality toward risk of PNF and allows discarding of unsafe organs from the donor organ pool in order to avoid futile liver transplantations. The term "and/or" relates to measurement of: NGA2F alone, NGA2FB alone, NG1A2F alone, NGA2F and NGA2FB, NGA2F and NG1A2F, NGA2FB and NG1A2F, or, NGA2F and NGA2FB and NG1A2F in order to avoid futile liver transplantations.

This disclosure thus relates in a first instance to a process of predicting the appearance of primary non function of a liver graft comprising:
obtaining a liver,
collecting a perfusate from the liver, and
determining the relative abundance of the agalactosylated, core-α-1,6-fucosylated biantennary N-glycan (NGA2F) in the total N-glycan profile within the perfusate, and/or the relative abundance of the agalactosylated, core-α-1,6-fucosylated bisecting biantennary N-glycan (NGA2FB) in the total N-glycan profile within the perfusate and/or the relative abundance of the mono galactosylated, core-α-1,6-fucosylated biantennary N-glycans (NG1A2F) in the total N-glycan profile within the perfusate wherein a significantly increased amount of NGA2F, NGA2FB or NG1A2F compared to the amount of, respectively, NGA2F, NGA2FB or NG1A2F in a perfusate collected from a control liver, is predictive for the appearance of primary non function of a liver graft.

The term "PNF" is defined as the absence of initial function following transplantation. Such evidence would include not only frank signs of total hepatic failure (e.g., profound hypoglycemia, uncorrectable coagulopathy, stage IV coma, renal failure, acidosis, and cardiodynamic shock), but also other signs of irreparable damage to the organ (i.e., massive rises in transaminases along with unrelenting daily rises in bilirubin, persistent renal insufficiency, mental confusion and persistent coagulopathy).

The terms "predict the appearance of primary non function of a liver graft" relates to forecasting in a reliable manner whether a donor liver will develop PNF after transplantation.

The terms "obtaining a liver" relate to well-known practices to procure and transport donor livers that will be transplanted. This disclosure thus relates to an "in vitro" diagnostic method applied on a liver after the liver has been removed from a human or animal body and before the liver will be transplanted in another human or animal body.

The terms "collecting a perfusate" relate to flushing the liver with the solution in which the donor liver is transported and subsequently collecting the solution, which then comprises proteins produced by liver cells. Non-limiting examples of solutions to transport livers are Histidine-tryptophan-ketoglutarate (Custodiol HTK, Essential Pharmaceuticals, LLC, Pennsylvania, USA) or Wisconsin solution (Viaspan, Duramed Pharm. Inc., Pomona, N.Y.). A more detailed but non-limiting example of how to collect a perfusate is given further in the Examples section below.

The term "the N-glycan-agalacto-core-alpha-1,6-fucosylated biantennary oligosaccharide (NGA2F)" refers to an asialo, agalacto, fucosylated biantennary oligosaccharide-type structure:

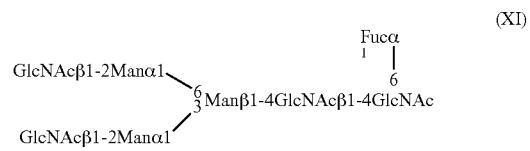

The term "the N-glycan agalactosylated, core-α-1,6-fucosylated bisecting biantennary oligosaccharide (NGA2FB)" refers to an asialo, agalacto, fucosylated bisecting biantinnary oligosaccharide-type structure:

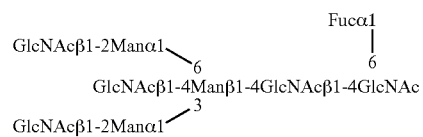

The term "the N-glycan mono galactosylated, core-α-1,6-fucosylated biantennary oligosaccharide (NG1A2F)" refers to an asialo, mono galactosylated, fucosylated biantennary oligosaccharide-type structure:

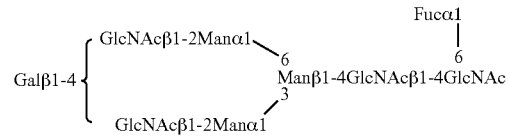

The terms "determining the relative abundance of NGA2F/NGA2FB/NG1A2F in the total N-glycome profile" relates to any method known to (relatively) quantify the presence of NGA2F, NGA2FB or NG1A2F molecules within the perfusate. Specifically, the latter terms refer to "determining the amount of NGA2F NGA2FB or NG1A2F via capillary electrophoresis" and, more specifically, the latter terms refer to "determining the amount of NGA2F, NGA2FB or NG1A2F via DNA sequencer-assisted fluorophore-assisted capillary electrophoresis" as is described by Callewaert et al. (2004 Nat. Med. 429).[10] Other techniques can be used for quantification/profiling of glycans including MALDI-TOF Mass spectrometry, high-performance anion-exchange chromatography with pulsed amperometric detection, High Performance Liquid chromatography and Lectin Array.

The preparation and labeling of the glycans in perfusate for sequencing can be performed using the on-membrane deglycosylation method described by Laroy et al.[15] An in-solution deglycosylation method has been developed for serum glycan profiling in a clinical context (sample preparation time less than 2 hours). As a high sample volume of the perfusate (more than 200 μL) is needed for the on-membrane deglycosylation method (compared to <10 μL serum) the samples have to be concentrated before applying the in-solution deglycosylation assay.

The terms "a significantly increased amount of NGA2F, NGA2FB or NG1A2F, compared to the amount of NGA2F, NGA2FB or NG1A2F, respectively, in a perfusate collected from a control liver" means an increase of relative abundance of the cited N-glycan in relation to the total N-glycome profile.

The cut-off value of 10.8% is based on the difference between NGA2F abundance in PNF and non-PNF patients' glycomes. No overlap was observed (FIG. 3). A C4.5 algorithm[16] was used to determine this cut-off and confirm the correct classification of all cases (FIG. 4). A C4.5 is an algorithm used to generate a decision tree and can be used for classification of subsets in a dataset. In this application, patients were classified as having PNF or no PNF according to the relative abundance of NGA2F in relation to the total N-glycome profile in perfusate.

Hence, this disclosure relates to a process as described above wherein determining the relative amount of NGA2F, NGA2FB or NG1A2F within the perfusate is undertaken by capillary electrophoresis.

More specifically, this disclosure relates to a process as described above wherein capillary electrophoresis is DNA sequencer-assisted fluorophore-assisted capillary electrophoresis.

This disclosure further relates to a process as described above wherein capillary electrophoresis is undertaken on N-glycans, which are released from proteins present in the perfusate and are subsequently derivatized in order to allow their detection and/or quantification/profiling.

Hence, this disclosure relates to a process as described above wherein derivatization comprises—as non-limiting examples—labeling of N-glycans with 8-aminopyrene-1,3,6-trisulphonic acid and/or desialylation. It should be clear, depending on the methodology used, that other labels can be used as well.

This disclosure further relates to a process as described above wherein the control liver is a liver that, after transplantation, does not result in the appearance of primary non function.

This disclosure also relates to a process as described above wherein the perfusate of the liver is concentrated before the relative abundance of N-glycans is determined.

This disclosure thus also relates in essence to the usage of the N-glycan NGA2F, NGA2FB and/or NG1A2F to predict the appearance of primary non function of a liver graft.

This disclosure will now be further illustrated by the following non-limiting examples.

BRIEF DESCRIPTION OF THE DRAWINGS

FIG. 5A, N-glycan profile in perfusate. FIG. 5B, N-glycan profile in human serum. FIG. 5C, characterization of N-glycan profile in human serum.

FIGS. 6A-6D present an example of the total protein N-glycans profile with the non-concentrated LTX 100 sample (FIG. 6A), the concentrated sample with the 10 kDa filter (FIG. 6B), and the two controls, the Filtrate after the concentrating step of the LTX 100 sample (FIG. 6C), and the blank sample that is preservation fluid (FIG. 6D).

DETAILED DESCRIPTION

Examples

Materials and Methods

Patients

Figure 1:
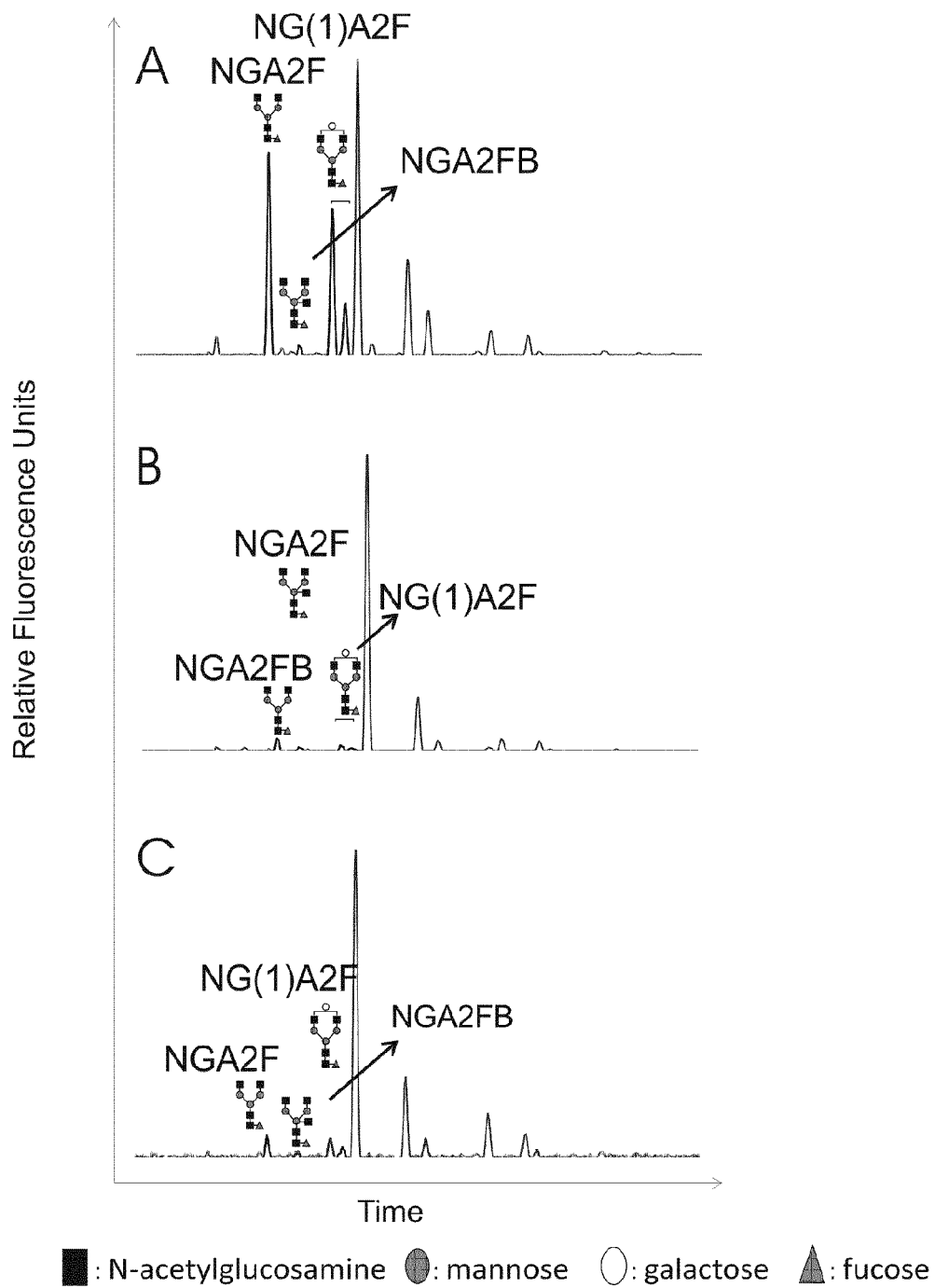
FIG. 1: Example of a whole N-glycan profile obtained using DNA sequencer-aided fluorophore-assisted carbohydrate electrophoresis (DSA-FACE). The relative abundance of NGA2F, NGA2FB and NG1A2F in the total N-glycome profile are increased in perfusate of PNF patients (Panel A—peaks 3 and 4 are isomers), but not in patients without PNF (Panel B). Furthermore, a patient who suffered a hepatic artery thrombosis early after transplantation, necessitating urgent retransplantation, showed no increase of NGA2F, NGA2FB and NG1A2F (Panel C).

From October 2011 until July 2013, 85 orthotopic liver transplantations were performed in 74 adult patients at Ghent University Hospital. In this cohort of patients, preservation solution from 54 liver transplantations in 52 patients could be sampled prospectively.

PNF was defined as the need for urgent retransplantation when a graft never demonstrated any evidence of initial function following transplantation after exclusion of other causes like hepatic artery thrombosis or acute cellular rejection. It was typically accompanied by high transaminases, low PT and high bilirubin.

Sample Collection and Processing

The preservation solution was obtained during the back-table procedure. Liver grafts were procured according to local practices and transported to the center in Histidine-tryptophan-ketoglutarate (Custodiol HTK, Essential Pharmaceuticals, LLC, Pennsylvania, USA) or Wisconsin solution (Viaspan™, Duramed Pharm. Inc., Pomona, N.Y.). During the back-table procedure, the left portal vein was flushed with a syringe of 20 ml of perfusate in which the graft was transported under normal hydrostatic pressure. Perfusates were collected and immediately stored at −21° C.

N-Glycosylation Analysis

Perfusate samples were prepared using the 96-well on membrane deglycosylation method, that has been previously described in detail.[9, 15] In summary, proteins in 500 µl of preservation solution were denatured using 1 ml of denaturing buffer and subsequently loaded on a 96-well plate containing methanol-activated PVDF membrane. The bound proteins are subsequently reduced and carboxymethylated before digestion with Peptide N-glycosidase F to release the N-glycans. The N-glycans are then labeled with 8-aminopyrene-1,3,6-trisulphonic acid and the excess of label is removed using size exclusion chromatography (Sephadex G-10 resin). A fraction of the sample is then desialylated and then analyzed with an ABI 3130 DNA sequencer. A desialylated serum protein N-glycan profile was obtained for the study objects. Thirteen peaks that were detectable in all samples were quantified using Peak Scanner 2 Version 2.0 software (Applied Biosystems, Foster City, Calif., USA), and normalized their abundance to the total peak height intensity. The nature of these peaks has been identified before by structural analysis.[10]

DRI was calculated according to Feng et al.[3] using the online calculator (gastro.cchmc.org/calculator/donor-risk-index). Eurotransplant DRI (ET-DRI) was calculated according to Braat et al.[4]

Statistical Analysis

SPSS 22.0 was used. Groups were compared using Mann Whitney U test. Glycome expressions were compared between PNF and non PNF patients. Differences were studied using logistic regression with forward stepwise selection in order to identify discriminating abundance profiles of glycans.

Results

1) Patient Population

N-glycan analysis was performed in perfusate from 54 liver transplantations in 52 patients. Three patients developed a PNF. Two more patients needed an urgent re-transplantation, both due to hepatic artery thrombosis, and were not considered as PNF. Patient characteristics are summarized in Table 1. Significant differences were observed between the PNF and non PNF patients regarding recipient ALT, AST and INR levels 48 hours after transplantation, reflecting the presence of a PNF. Interestingly, use of DCD donors or choice of perfusion fluid was not related to PNF. In the cohort, DRI could not predict PNF.

TABLE 1

Patient Characteristics

|  | No PNF (n = 51) | PNF (n = 3) | Total (n = 54) | p-value |
|---|---|---|---|---|
| Recipient Characteristics | | | | |
| Demographic data | | | | |
| Age (SD) | 53.5 (13.9) | 43.5 (21.9) | 51 (14.1) | n.s. |
| Sex (M/W) | 30/21 | 2/1 | 32/22 | |
| Biochemical data | | | | |
| AST at 48 hours (U/L) (SD) | 643 (1072) | 7536 (4810) | 626 (1780) | 0.01 |
| ALT at 48 hours (U/L) (SD) | 522 (851) | 6710 (7793) | 535 (1773) | 0.07 |
| INR | 1.62 (1.17) | 12.5 (11.2) | 1.64 (2.79) | 0.06 |
| Total bilirubin (mg/dl) (SD) | 2.7 (4.95) | 7.56 (6.27) | 3 (4.77) | n.s. |
| Donor Characteristics | | | | |
| Age (SD) | 46.5 (17.2) | 57.5 (19.19) | 46.5 (17.14) | n.s. |
| Sex (M/W) | 27/24 | 2/1 | 29/25 | |
| Length (cm) (SD) | 172 (7.05) | 160 (11.5) | 171 (7.8) | n.s. |
| Weight (cm) (SD) | 78 (17.9) | 60 (6.36) | 75.5 (18.1) | n.s. |
| Perfusate (HTK/UW) | 41/10 | 2/1 | 43/11 | |
| CIT (minutes) (SD) | 399 (120) | 493 (10) | 399 (120) | n.s. |
| WIT (minutes) (SD) | 38 (16) | 40 (11) | 37 (15) | n.s. |
| AST (U/L) (SD) | 42 (54) | 22 (3) | 41.5 (51) | n.s. |
| ALT (U/L) (SD) | 32 (34) | 25 (19) | 32 (34) | n.s. |
| GGT (mg/dl) (SD) | 41 (96) | 20 (8) | 37 (93) | n.s. |
| Total Bilirubin (mg/dl) (SD) | 0.62 (5.82) | 0.72 (0.16) | 0.64 (5.55) | n.s. |
| DCD | 2 | 0 | 2 | |
| DRI (SD) | | | | |
| ET-DRI (SD) | 1.67 (0.38) | 1.71 (0.35) | 1.67 (0.37) | n.s. |

Variables are expressed as means followed by standard deviation between brackets.

Abbreviations: CIT: Cold Ischemia Time; DCD: Donation after Cardiac Death; DRI: Donor Risk Index; ET: Eurotransplant; PNF: Primary Non Function; HTK: Histidine-Tryptophan-Ketoglutarate; n.s.: Non Significant; SD: standard deviation; UW: University of Wisconsin Solution; WIT: Warm Ischemia Time 2) N-Glycan Analysis on Total Amount of Glycoproteins in Perfusate is Feasible The technique used for N-glycan analysis is based on a DNA sequencer-assisted fluorophore-assisted capillary electrophoresis that was initially developed and validated for serum analysis[10] but has been successfully used for samples of diverse nature including urine analysis.[17]

Now, this technique was applied on perfusate from liver transplant patients. Using the standard protocol, electropherograms of high quality were obtained. Electropherograms are comparable to those obtained on serum and show 13 peaks. Each peak has been identified to be the same N-glycan structure as previously described in serum.

3) N-Glycan Analysis of Perfusate can Predict the Appearance of PNF

Figure 2:
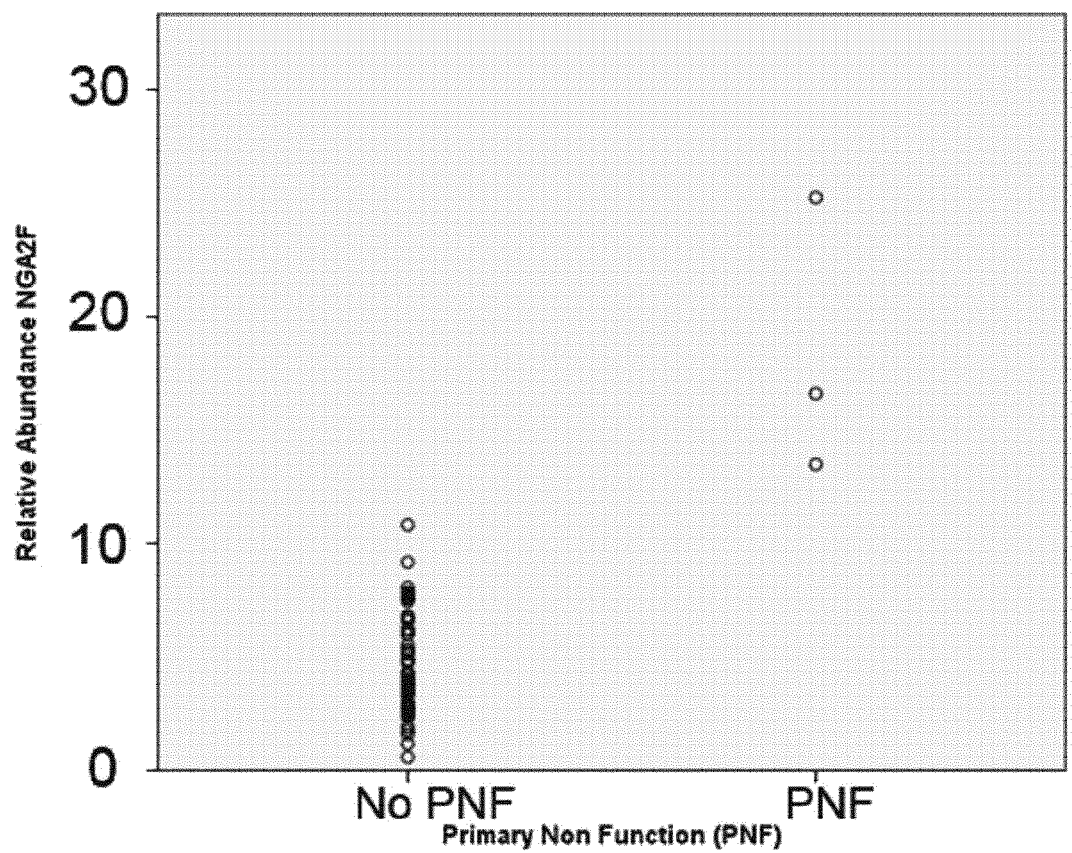
FIG. 2: Relative abundance of NGA2F in the total N-glycome profile is increased in perfusate of PNF patients and can predict PNF.
Figure 3:
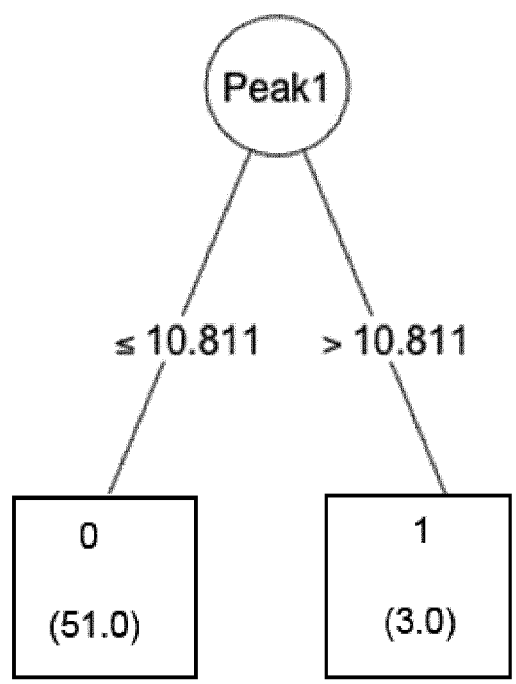
FIG. 3: Classification of patients using a C4.5 algorithm discriminates between PNF and non-PNF liver transplant recipients using a cut-off for NGA2F of 10.8.
Figure 4:
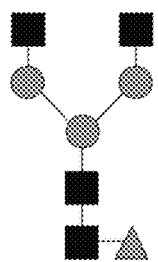
FIG. 4: Schematic representations of the N-glycans of this disclosure: agalactosylated, core-α-1,6-fucosylated biantennary N-glycan (NGA2F); agalactosylated, core-α-1,6-fucosylated bisecting biantennary N-glycan (NGA2FB); mono galactosylated, core-α-1,6-fucosylated biantennary N-glycans (NG1A2F).
Figure 4:
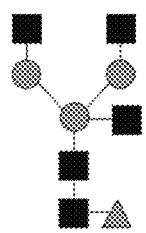
Figure 4:
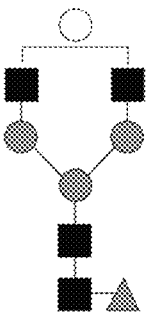

In the cohort of 54 patients, five patients needed an urgent re-transplantation, three due to PNF and two due to hepatic artery thrombosis (HAT). Interestingly, an increase in the relative abundance of peak 1 was observed in all PNF patients but not in the HAT patients (FIG. 1). Peak 1 has been characterized to be NGA2F, a biantennary core fucosylated glycan. Using a cut-off of 10.8% for the relative abundance of NGA2F on perfusate, unequivocal classification of all three PNF patients and prediction of the appearance of PNF before liver transplantation were successful (FIG. 2). Increase of relative abundance of NGA2FB and NG1A2F was also observed in PNF patients.

Levels of ALT in Perfusate are not Related to PNF

ALT levels were analyzed in perfusate. An increase of these values in perfusate of PNF patients was not observed.

Steatosis of the donor liver graft is a risk factor for PNF but is not predictive for PNF.

Figure 7:
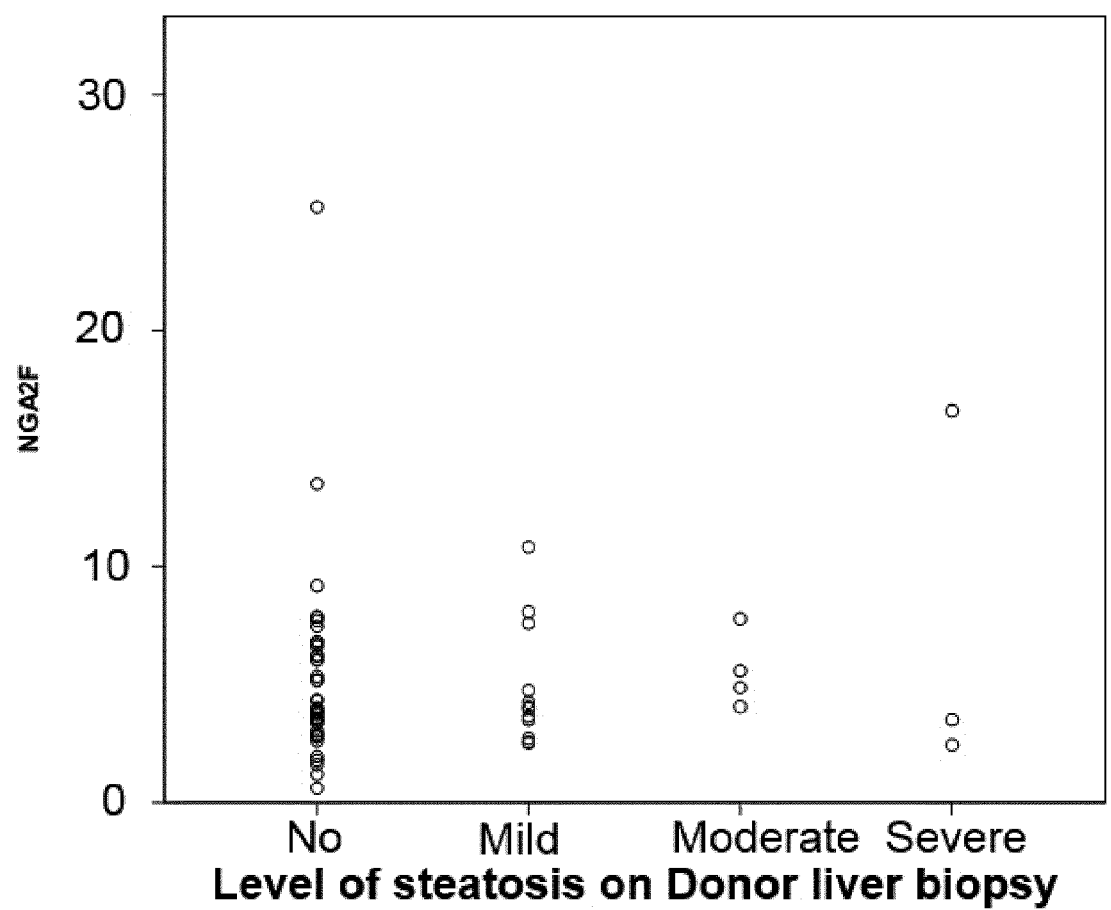
FIG. 7: Steatosis is not predictive for the occurrence of PNF (peak 1 represents NGA2F).

In this cohort, the presence of steatosis was not related to the relative abundance of peak 1 (=NGA2F) (FIG. 7). In contrast, the relative abundance of NGA2F was 100% predictive for the occurrence of PNF.

In this cohort, three patients developed PNF. Only one of them had severe steatosis. Both other patients had no steatosis at all. Two other patients with severe steatosis did not develop PNF.

Further Optimization of the Glycan Analysis of this Disclosure

The procedure of sample preparation and glycan labeling can be further optimized in order to increase the speed of turn over time to 2 hours rather than the current 2 days.

For example, the preparation and labeling of the glycans in perfusate for sequencing can be performed using the on-membrane deglycosylation method described by Laroy et al., 2006. An in-solution deglycosylation method has indeed been developed for serum glycan profiling in a clinical context (sample preparation time less than 2 hours). As a high sample volume of the perfusate (more than 200 µL) is needed for the on-membrane deglycosylation method (compared to <10 µL serum), the samples have to be concentrated before applying the in-solution deglycosylation assay.

The present technique is not only performed on DNA sequencers, but also routine capillary electrophoresis devices that are available in routine clinical labs can be used, as has been achieved for serum glycan analysis.

Further Optimization of the Glycan Analysis of this Disclosure (II)

Materials and Methods

Samples Collection

Samples in perfusate fluid have been collected during liver transplantation of each patient. The first perfusate sample (noted as "CONTAINER") of the container was sampled after preparation of the liver and flushing of the hepatic artery with perfusate liquid. The second sample (noted as "VEIN") was collected after flushing the left hepatic vein using a 20 mL syringe with 20 mL perfusate liquid. The third sample (noted as "BILIARY TRACT") was collected in the container after flushing the biliary tract with 20 mL perfusate liquid. All samples were collected in 15 mL tubes and immediately stored at −20° C. in a freezer without any further manipulation.

Pre-Analysis Steps

Concentrating Step

The human samples in preservation fluid were concentrated in order to obtain a protein concentration in the fluid that is similar to serum. The protocol was as follows: Each human sample in the preservation fluid was centrifuged 10 minutes at 2000 g in the Eppendorf Centrifuge 5424, in order to spin down the debris. The Amicon Ultra-0.5 Centrifugal Filter Device was inserted into one of the provided microcentrifuge tubes and 500 μL of sample was added. The capped filter device was spun at 14,000 g for 30 minutes. The concentrated sample was collected by reverse spin into a new microcentrifuge tube, by placing the Amicon Ultra filter device upside-down and spinning for 2 minutes at 1,000 g. In samples that needed an extra concentrating step, 10 μL of concentrated sample was refilled in a new Amicon Ultra-0.5 Centrifugal Filter Device and the entire procedure was repeated.

Determination of the Protein Concentration

The Bio-Rad DC Protein Assay is a colorimetric assay for protein concentration following detergent solubilization. The optimized protocol for samples in perfusate fluid is as follows: A Standard curve until 2 mg/mL was prepared with BSA in perfusate fluid. An initial solution of 100 mg/mL BSA in perfusate fluid was prepared. By dilution 50×, the standard solution of 2 mg/mL was obtained (Standard 51). From 51 by diluting 2× the standard curve of 1 mg/mL (S2), 0.5 mg/mL (S3), 0.25 mg/mL (S4), 0.125 mg/mL (S5) 0.0625 mg/mL (S6) and blank (S7) was prepared. Human Samples were diluted 5×, 10× and 20× in perfusate fluid. Five μL of standard BSA or diluted sample in perfusate fluid was added in a 96-well plate with flat bottom (not curved). Twenty-five μL of reagent A' that was previously prepared in an Eppendorf was added and 200 μL of reagent B. The plate was incubated 15 minutes at RT in the dark and the absorbance was measure at 690 nm. The protein concentration of each human sample in perfusate fluid was determined according to the measured standard curve.

Protein N-Glycome Sample Processing

The N-glycans present on the proteins in 3 μl of the concentrated samples were released after protein binding to a 96-well PCR plate, derivatized with 8-aminopyrene-1,3, 6-trisulfonic acid (APTS), desialylated and analyzed by DSA-FACE (DNA sequencer-assisted fluorophore-assisted carbohydrate electrophoresis, Applied Biosystems). The optimized protocol for glycan release and labeling using a PCR thermocycler is as follows: 2 μl of 10 mM NH$_4$Ac buffer, pH 5 containing 3.5% SDS were added to 3 μL of sample in 96-well PCR plate. Each sample was mixed by up and down pipetting without creating any bubbles. The tightly closed tubes were centrifuged for 1 minute at 335 g and heated at 95° C. for 5 minutes in a standard PCR thermocycler with heated lid. After cooling in ice, 5 μl of 10 mM NH$_4$Ac, pH 5, containing 2% NP-40 solution and 2.5 IUBMB milliunits of peptide N-glycosidase F (PNGase F, Glyko) were added. The tubes were mixed, centrifuged and incubated in the PCR thermocycler for 10 minutes at 37° C. with lid closed at 40° C. Subsequently, 5 μl of 100 mM NH$_4$Ac, pH 5 with 40 milliunits of α(2→3,6,8,9)-sialidase were added, followed by up and down mixing. The tubes were tightly closed, centrifuged and incubated in the PCR thermocycler for 60 minutes at 37° C. with lid closed at 40° C. Following the incubation, samples were evaporated to dryness, for 20 minutes at 80° C. with tubes open. The evaporation was complete, after which 5 μl of the labeling solution (1:1 solution of 200 mM APTS in 1.2 M citric acid and 1 M NaBH$_3$CN in DMSO) were added to the bottom of the tubes. The tightly closed tubes were vortexed and heated at 50° C. for 2 hours. The elevated temperature ensures fast reaction kinetics. The reaction was quenched with 200 μL water. 20 μL of the resulting solutions were used for analysis by DSA-FACE. Data analysis was performed using the GeneMapper software v3.7 (Applied Biosystems). The heights of 12 peaks in all samples were quantified to obtain a numerical description of the profiles and the data was analyzed.

Materials

Ammonium Acetate (NH$_4$Ac), Sodium Dodecyl sulphate (SDS), citric acid, Sodium cyanoboro hydride 95% (NaBH$_3$CN), Dimethyl sulfoxide (DMSO) and APTS (8-Aminopyrene-1,3,6-trisulfonic acid 3 and Bovine Serum Albumin (BSA) were purchased by Sigma Aldrich. Nonidet-40 (NP-40) was purchased by Fluka Biochemika. The 96-well PCR plates, non-skirted, were purchased by Thermo Scientific and the MicroAmp Optical 96-Well Reaction Plate by Applied Biosystems. The enzymes *Arthrobacter ureafaciens* α(2→3,6,8,9)-sialidase (200 mU/μL) and PNGase F (600 U/μL NEB) were prepared by the department of Medical Biotechnology Center (VIB, UGent). The colorimetric assay (DC Protein Assay) for protein concentration was purchased by BioRad. Amicon Ultra-0.5 Centrifugal Filter Devices of 10K (10,000 NMWL), 30K (30,000 NMWL), 50K (50,000 NMWL) and 100K (100,000 NMWL) were purchased by Merck Millipore Ltd.

Results

Pre-analysis steps

Concentrating Step

The human samples in preservation fluid were concentrated in order to obtain a protein concentration in the fluid that is similar to serum. The volumes obtained were quite low (around 15-20 For all samples with extra concentrating step, only 10 μL were used because the volume was low. The final extra concentrated samples (i.e., 2×) was quite viscous.

Total Serum Protein N-Glycan Profiles

High protein concentration was needed for the in-solution deglycosylation protocol that was optimized for serum (used for detecting the N-glycans). The obtained N-glycan profile of the concentrated samples in preservation fluid were compared with the typical N-glycan profile from the total human serum proteins that was obtained with the traditional on-membrane deglycosylation.

Figure 5A:
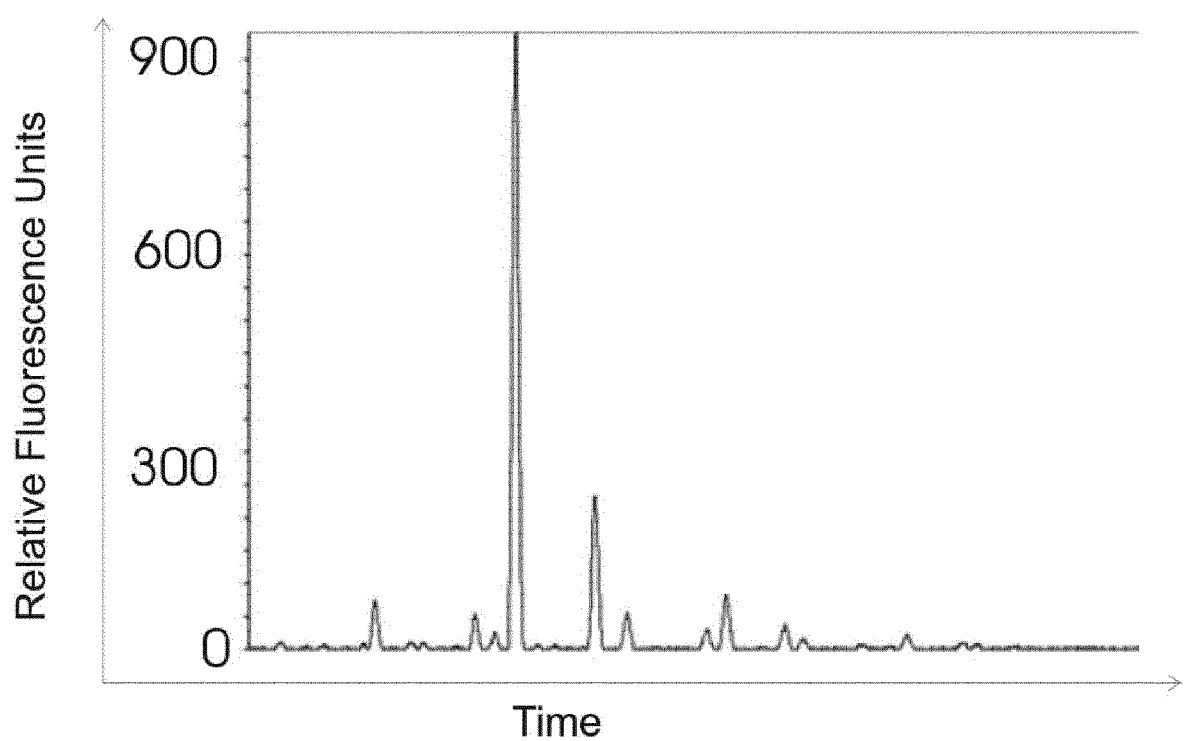
FIGS. 5A-5C: The N-glycan profile of the concentrated samples in perfusate were comparable with the typical N-glycan profile from the total human serum proteins.
Figure 5B:
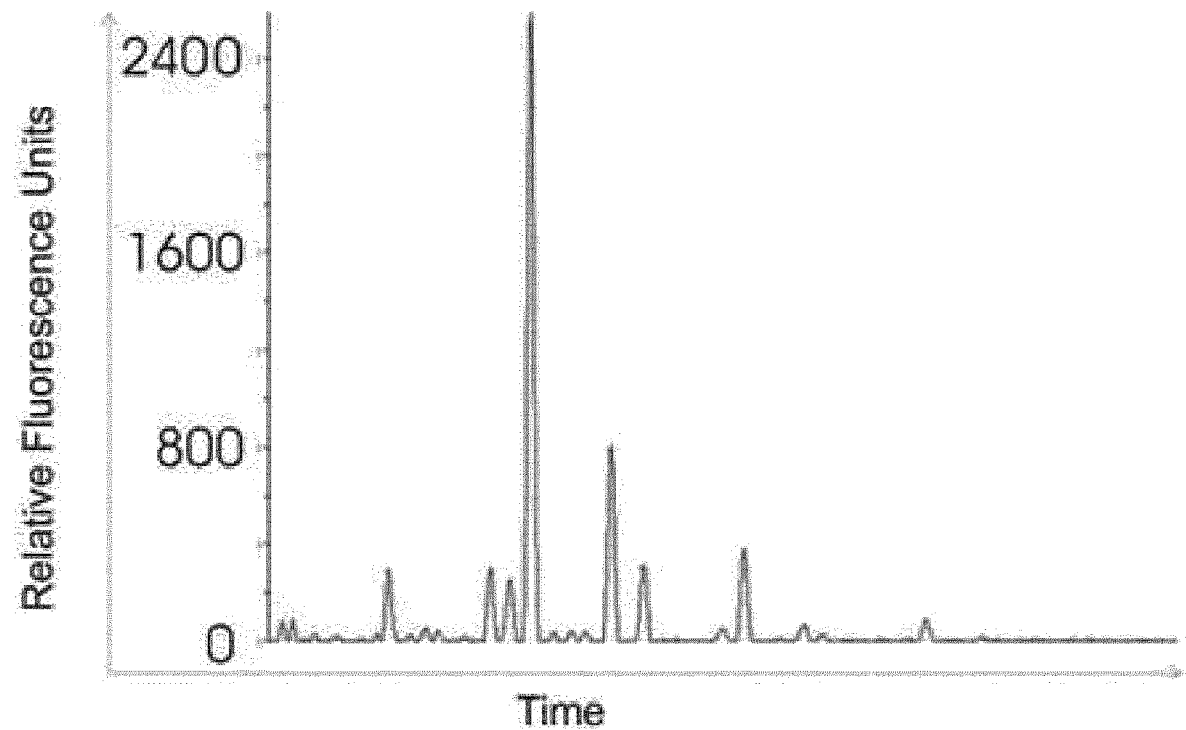
Figure 5C:
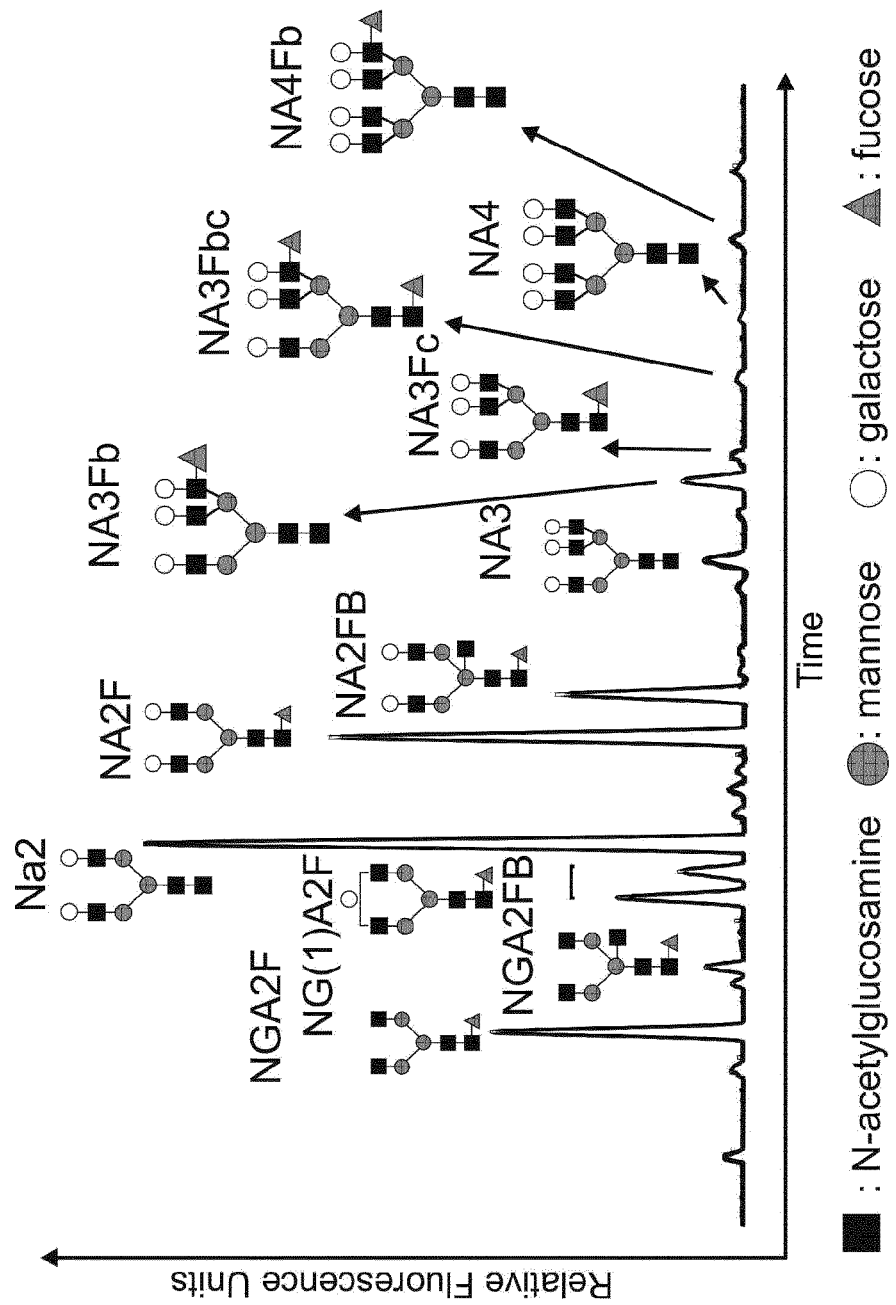

A desialylated protein N-glycan profile was obtained for samples in preservation fluid from liver transplant patients. The total protein N-glycans profile of the concentrated (LTX 100) in preservation fluid sample (FIGS. 5A-5C) was similar with the usual profile of the total human serum proteins.

All filters used (10, 30, 50 and 100 kDa) presented a similar profile, with NA2 relative fluorescent intensity of 1621, 1569, 1689 and 2817 for 10, 30, 50 and 100 kDa filters used (Table 2).

TABLE 2

Results of the relative fluorescent intensity for the TEST 3 concentrating step for sample LTX 100 in preservation fluid.

| Test 3 concentrating perfusate | Height peaks | | | | | | |
|---|---|---|---|---|---|---|---|
| | 1 NGA2F | 2 NGA2FB | 3 NG1A2F1 | 4 NG1A2F2 | 5 NA2 | 6 NA2F | 7 NA2FB |
| 100-not conc dilution 1/125 | | | | | 47 | | |
| 100-(10) dilution 1/125 | | | | | 308 | | |
| 100-(30) dilution 1/125 | | | | | 795 | | |
| 100-(50) dilution 1/125 | | | | | 993 | | |
| 100-(100) dilution 1/125 | | | | | 1207 | | |
| C-_(10ex) dilution 1/125 | | | | | no peak | | |
| C-_(100ex) dilution 1/125 | | | | | no peak | | |
| 100-(10ex) dilution 1/125 | | | | | 429 | | |
| 100-(30ex) dilution 1/125 | | | | | 1305 | | |
| 100-(50ex) dilution 1/125 | | | | | 868 | | |
| 100-(100ex) dilution 1/125 | | | | | 1024 | | |
| 100-(10) F dilution 1/125 | | | | | no peak | | |
| 100-(30) F dilution 1/125 | | | | | no peak | | |
| 100-(50) F dilution 1/125 | | | | | no peak | | |
| 100-(100) F dilution 1/125 | | | | | no peak | | |
| only APTS dilution 1/125 | | | | | no peak | | |
| 100-not conc quenched | | | | | 252 | | |
| 100-(10) quenched | 146 | 21 | 156 | 1228 | 1621 | 323 | 59 |
| 100-(30) quenched | 146 | 21 | 153 | 1155 | 1569 | 308 | 54 |
| 100-(50) quenched | 154 | 23 | 143 | 1097 | 1689 | 329 | 64 |
| 100-(100) quenched | 239 | 35 | 274 | 2541 | 2817 | 523 | 89 |
| C-_(10ex) quenched | | | | | 20 | | |
| C-_(100ex) quenched | | | | | 26 | | |
| 100-(10ex) quenched | SS | 8 | 99 | 569 | 1250 | 182 | 45 |
| 100-(30ex) quenched | 203 | 33 | 392 | 2117 | 3775 | 602 | 117 |
| 100-(50ex) quenched | 164 | 20 | 260 | 1248 | 2543 | 410 | 97 |
| 100-(100ex) quenched | 200 | 22 | 328 | 1175 | 3240 | 524 | 128 |
| 100-(10) F quenched | | | | | 17 | | |
| 100-(30) F quenched | | | | | no peak | | |
| 100-(50) F quenched | | | | | 31 | | |
| 100-(100) F quenched | | | | | 35 | | |
| only APTS quenched | | | | | no peak | | |

| Test 3 concentrating perfusate | Height peaks | | | | | | Normalized peak heights |
|---|---|---|---|---|---|---|---|
| | 8 NA3 | 9 NA3Fb | 9' NA3Fc | 10 NA3Fbc | 11 NA4 | 12 NA4Fb | (% of total) Total |
| 100-not conc dilution 1/125 | | | | | | | 47 |
| 100-(10) dilution 1/125 | | | | | | | 308 |
| 100-(30) dilution 1/125 | | | | | | | 795 |
| 100-(50) dilution 1/125 | | | | | | | 993 |
| 100-(100) dilution 1/125 | | | | | | | 1207 |
| C-_(10ex) dilution 1/125 | | | | | | | 0 |
| C-_(100ex) dilution 1/125 | | | | | | | 0 |
| 100-(10ex) dilution 1/125 | | | | | | | 429 |
| 100-(30ex) dilution 1/125 | | | | | | | 1305 |
| 100-(50ex) dilution 1/125 | | | | | | | 868 |
| 100-(100ex) dilution 1/125 | | | | | | | 1024 |
| 100-(10) F dilution 1/125 | | | | | | | 0 |
| 100-(30) F dilution 1/125 | | | | | | | 0 |
| 100-(50) F dilution 1/125 | | | | | | | 0 |
| 100-(100) F dilution 1/125 | | | | | | | 0 |
| only APTS dilution 1/125 | | | | | | | 0 |
| 100-not conc quenched | | | | | | | 252 |
| 100-(10) quenched | 143 | 98 | 96 | 46 | 22 | 13 | 3972 |
| 100-(30) quenched | 37 | 91 | 97 | 45 | 21 | 9 | 3806, 266667 |
| 100-(50) quenched | 133 | 89 | 105 | 42 | 20 | 11 | 3899 |
| 100-(100) quenched | 286 | 202 | 163 | 97 | 48 | 19 | 7333 |
| C-_(10ex) quenched | | | | | | | 20 |
| C-_(100ex) quenched | | | | | | | 26 |
| 100-(10ex) quenched | 71 | 41 | 63 | 16 | 15 | 11 | 2425 |

TABLE 2-continued

Results of the relative fluorescent intensity for the TEST 3 concentrating step for sample LTX 100 in preservation fluid.

| | | | | | | | |
|---|---|---|---|---|---|---|---|
| 100-(30ex) quenched | 237 | 164 | 197 | 63 | 34 | 17 | 7951 |
| 100-(50ex) quenched | 154 | 100 | 129 | 35 | 13 | 12 | 5185 |
| 100-(100ex) quenched | 154 | 91 | 172 | 40 | 9 | 16 | 6099 |
| 100-(10) F quenched | | | | | | | 17 |
| 100-(30) F quenched | | | | | | | 0 |
| 100-(50) F quenched | | | | | | | 31 |
| 100-(100) F quenched | | | | | | | 35 |
| only APTS quenched | | | | | | | 0 |

Figure 6:
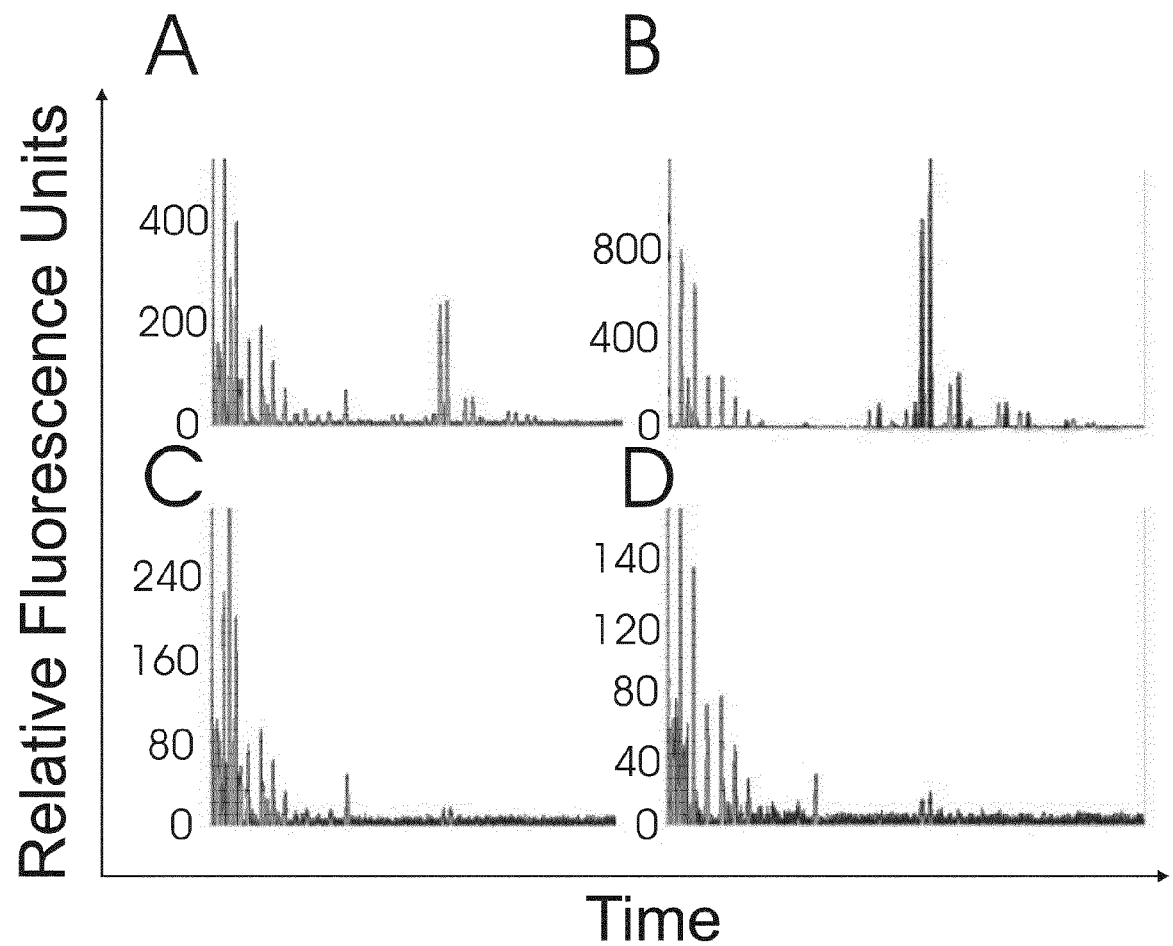
FIGS. 6A-6D: Concentration of perfusate enables analysis of the N-glycan profile using the in-solution method.

*100 = Perfusate LTX 100
*C- = Control negatif (perfusate fluid)
*F- = Filtrate
*ex = extra concentrating step of 10 µL concentrated sample However, the LTX 100 in preservation fluid was concentrated approximately 6× with the 10, 30, 50 kDa filters and 11× with the 100 kDa filters. FIGS. 6A-6D present an example of the total protein N-glycans profile with the non-concentrated LTX 100 sample (FIG. 6A), the concentrated sample with the 10 kDa filter (FIG. 6B), and the two controls, the Filtrate after the concentrating step of the LTX 100 sample (FIG. 6C), and the blank sample that is preservation fluid (FIG. 6D).

No height peak (i.e., 20-26 for NA2) in the blank (preservation fluid) was observed. The filtrates presented a height peak in the baseline (i.e., 0-35 for NA2), which explains that there is not any significant loss of protein during the concentrating procedure. The dilution 1/125 reduced the signal compared with the quenched initial plate. The use of the higher APTS concentration from 20 mM to 200 mM increased the fluorescent intensity signal (from previous Test 2: the NA2 was 121 before and 292 after the concentrating step).

REFERENCES

1. Shaw, B. W., R. D. Gordon, S. Iwatsuki, and T. E. Starzl. Hepatic Retransplantation. *Transplant. Proc.* 17, 264-271 (1985).
2. Oh, C.-K., R. B. Sawyer, S. J. Pelletier, T. L. Pruett, and H. A. Sanfey. Independent predictors for primary nonfunction after liver transplantation. *Yonsei Med. J.* 45, 1155-61 (2004).
3. Feng, S. et al. Characteristics associated with liver graft failure: the concept of a donor risk index. *Am. J. Transplant* 6, 783-90 (2006).
4. Braat, A. E. et al. The Eurotransplant donor risk index in liver transplantation: ET-DRI. *Am. J. Transplant* 12, 2789-96 (2012).
5. Devlin, J. et al. Relationship between early liver graft viability and enzyme activities in effluent preservation solution. *Transplantation* 60, 627-31 (1995).
6. Bronsther, O. L. et al. Effluent levels of hyaluronic acid can predict ultimate graft outcome after clinical liver transplantation: a prospective series. *Transplant. Proc.* 25, 1538-40 (1993).
7. Verhoeven, C. J. et al. Biomarkers to assess graft quality during conventional and machine preservation in liver transplantation. *J. Hepatol.* 61, 672-84 (2014).
8. Monbaliu, D. and J. Brassil. Machine perfusion of the liver: past, present and future. *Curr. Opin. Organ Transplant.* 15, 160-6 (2010).
9. Callewaert, N. et al. Total serum protein N-glycome profiling on a capillary electrophoresis-microfluidics platform. *Electrophoresis* 25, 3128-3131 (2004).
10. Callewaert, N. et al. Noninvasive diagnosis of liver cirrhosis using DNA sequencer-based total serum protein glycomics. *Nat. Med.* 10, 429-34 (2004).
11. Vanderschaeghe, D. et al. GlycoFibroTest is a highly performant liver fibrosis biomarker derived from DNA sequencer-based serum protein glycomics. *Mol. Cell. Proteomics* 8, 986-94 (2009).
12. Blomme, B. et al. N-glycan based biomarker distinguishing non-alcoholic steatohepatitis from steatosis independently of fibrosis. *Dig. Liver Dis.* 44, 315-22 (2012).
13. Blomme, B. et al. Serum protein N-glycosylation in paediatric non-alcoholic fatty liver disease. *Pediatr. Obes.* 7, 165-73 (2012).
14. Verhelst X., B. Blomme, A. Geerts, I. Colle, R. I. Troisi, X. Rogiers, N. Callewaert. V. V. H. Glycomics as a new tool for preservation fluid analysis in liver transplantation. in *Acta Gastroenterologica Belgica* A25 (2013).
15. Laroy, W., R. Contreras, and N. Callewaert. Glycome mapping on DNA sequencing equipment. *Nat. Protoc.* 1, 397-405 (2006).
16. Quinlan, J. in (Morgan Kaufman, 1993).
17. Vermassen, T. et al. Urinary prostate protein glycosylation profiling as a diagnostic biomarker for prostate cancer. *Prostate* 75, 314-22 (2015).

The invention claimed is:

1. A process of selecting a liver graft for transplantation, the process comprising:
    determining the amount of N-glycan asialo-agalacto-fucosylated biantennary oligosaccharide (NGA2F) and/or N-Glycan agalactosylated, core-α-1,6-fucosylated bisecting biantennary oligosaccharide (NGA2FB) and/or the N-glycan mono galactosylated, core-α-1,6-fucosylated biantennary oligosaccharide (NG1A2F) in a perfusate from the liver graft,
    comparing the amount of NGAF2 and/or NGAF2B and/or NG1A2F with the amount of NGAF2 and/or NGAF2B and/or NG1A2F in a perfusate from a control liver graft that is a liver graft that, after transplantation, does not result in primary non-function, and
    selecting the liver graft for transplantation, wherein the selected liver does not have an increased amount of NGAF2 and/or NGAF2B and/or NG1A2F in comparison to the amount determined in the control liver graft, respectively.

2. The process according to claim 1, wherein determining the amount of NGA2F, NGA2FB and NG1A2F within said perfusate is undertaken by capillary electrophoresis.

3. The process of claim 2, wherein the perfusate is concentrated before determining the amount of N-glycans.

4. The process according to claim 2, wherein said capillary electrophoresis is DNA sequencer-assisted fluorophore-assisted capillary electrophoresis.

5. The process of claim 4, wherein the capillary electrophoresis is undertaken on N-glycans that are released from proteins present in the perfusate, which are subsequently derivatized.

6. The process of claim 5, wherein derivatization comprises labeling the N-glycans with 8-aminopyrene-1,3,6-trisulphonic acid and/or desialylation.

7. The process of claim 4, wherein the perfusate is concentrated before determining the amount of N-glycans.

8. The process according to claim 2, wherein said capillary electrophoresis is undertaken on N-glycans that are released from proteins present in said perfusate, which N-glycans are subsequently derivatized.

9. The process of claim 8, wherein the perfusate is concentrated before determining the amount of N-glycans.

10. The process according to claim 8, wherein derivatization comprises labeling said N-glycans with 8-aminopyrene-1,3,6-trisulphonic acid and/or desialylation.

11. The process of claim 10, wherein the perfusate is concentrated before determining the amount of N-glycans.

12. The process according to claim 1, wherein said perfusate is concentrated before said amount of said N-glycans is determined.

13. A method of transplanting a liver graft into a subject, wherein the method comprises:
    before transplanting the liver graft into the subject, determining the amount of N-glycan(s) in a perfusate from the liver graft, wherein the N-glycan(s) is/are selected from the group consisting of N-glycan asialo-agalacto-fucosylated biantennary oligosaccharide ("NGA2F"), N-glycan agalactosylated, core-$\alpha$-1,6-fucosylated bisecting biantennary oligosaccharide ("NGA2FB"), N-glycan mono galactosylated, core-$\alpha$-1,6-fucosylated biantennary oligosaccharide ("NG1A2F"), and any combination thereof; and
    transplanting the liver graft into the subject,
    wherein the liver graft does not have an increased amount of NGA2F, NGA2FB, and/or NG1A2F compared to the amount of NGA2F, NGA2FB, and/or NG1A2F, respectively, in a perfusate collected from a control liver.

* * * * *